United States Patent [19]

Poston

[11] Patent Number: 5,766,838
[45] Date of Patent: Jun. 16, 1998

[54] LEUKOCYTE ADHESION ASSAY

[76] Inventor: Robin Poston, 11 Marlborough Crescent, Sevenoaks, Kent, TN 13 2HH, United Kingdom

[21] Appl. No.: 569,211

[22] PCT Filed: Jun. 14, 1994

[86] PCT No.: PCT/GB94/01279

§ 371 Date: Dec. 14, 1995

§ 102(e) Date: Dec. 14, 1995

[87] PCT Pub. No.: WO94/29720

PCT Pub. Date: Dec. 22, 1994

[30] Foreign Application Priority Data

Jun. 15, 1993 [GB] United Kingdom .................. 9312315

[51] Int. Cl.$^6$ .............................. C12Q 1/00; G01N 33/53
[52] U.S. Cl. .............. 435/4; 435/326; 435/7.21; 435/7.24; 435/7.2; 435/40.52; 435/40.5; 435/7.1; 436/63; 436/803; 128/668; 128/670; 128/672; 128/749
[58] Field of Search ...................... 514/8; 435/7.24, 435/7.21, 4, 7.2, 40.52, 40.5, 7.1, 326; 424/493, 85.8; 436/63, 803, 805; 128/668, 670, 672, 749

[56] References Cited

U.S. PATENT DOCUMENTS

| | | | |
|---|---|---|---|
| 4,925,678 | 5/1990 | Ranney | 424/493 |
| 4,935,234 | 6/1990 | Todd, III et al. | 424/85.8 |
| 5,108,759 | 4/1992 | Ranney | 424/493 |
| 5,166,133 | 11/1992 | Houston et al. | 514/8 |
| 5,217,870 | 6/1993 | Hession et al. | 435/7.24 |
| 5,503,982 | 4/1996 | Hendricks et al. | 435/7.21 |
| 5,514,555 | 5/1996 | Springer et al. | 435/7.24 |

OTHER PUBLICATIONS

DiCoreleto et al., J. Immunol., 143(ii), 3666–3672 (1989).
Gamble et al., J. Immunol., Methods, 109, 175–184 (1988).
Poston et al., Am. J. Pathol., 140(3), 665–673 (1992).
Stamper and Woodruff, J. Exp. Med., 144, 828–833 (1976).
Yednock et al., Nature, 356, 63–66 (1992).
Beekhuizen et al., J. Leukocyte Biol., 54, 363–378 (1993).
Bar–Shavit et al., J. Cell. Biol., 112(2), 335–344 (1991).
Allen M. Gown, et al., Human Atherosclerosis II. Immunocytochemical Analysis of the Cellular Composition of Human Atherosclerotic Lesions, Am. J. Pathol. Oct. 1986, 125, 191–207.
Yong–jian Geng et al., Interferon–gamma Inhibits Scavenger Receptor Expression and Foam Cell Formation in Human Monocyte–derived Macrophages, J. Clin. Invest. Apr. 1992, 89, 1322–1330.
Henry Beekhuizen et al., CD14 Contributes to the Adherence of Human Monocytes to Cytokine–Stimulated Endothelial Cells, J. Immunol. Dec. 1, 1991, 147, 3761–3767.
Henry Beekhuizen et al., Characterization of Monocyte Adherence to Human Macrovascular and Microvascular Endothelial Cells, J. Immunol. Jul. 15, 1990, 145, 510–518.
Allard C. van der Wal et al., Adhesion Molecules on the Endothelium and Mononuclear Cells in Human Atherosclerotic Lesions 1992, 141, 1427–1433, Dec. 1992.

*Primary Examiner*—Louise Leary
*Attorney, Agent, or Firm*—Steven J. Hultquist

[57] ABSTRACT

A method of assaying leukocyte binding to a tissue sample, which comprises contacting a arterial tissue sample at a temperature of at least 10° C. with a suspension of monocytes or a cell line having adhesion to arterial tissue similar to monocytes, and quantitating the number of bound cells over a defined area of tissue sample section. The assay allows agents which inhibit binding of monocytes to human vascular tissue to be identified, and the use of such agents is described in the therapy of atherosclerosis.

23 Claims, 3 Drawing Sheets

SELECTIVE U937 CELL BINDING
TO ATHEROSCLEROTIC AREAS OF ARTERY

EFFECT OF RGD PEPTIDE ON U937 CELL ADHESION TO ATHEROSCLEROTIC PLAQUES

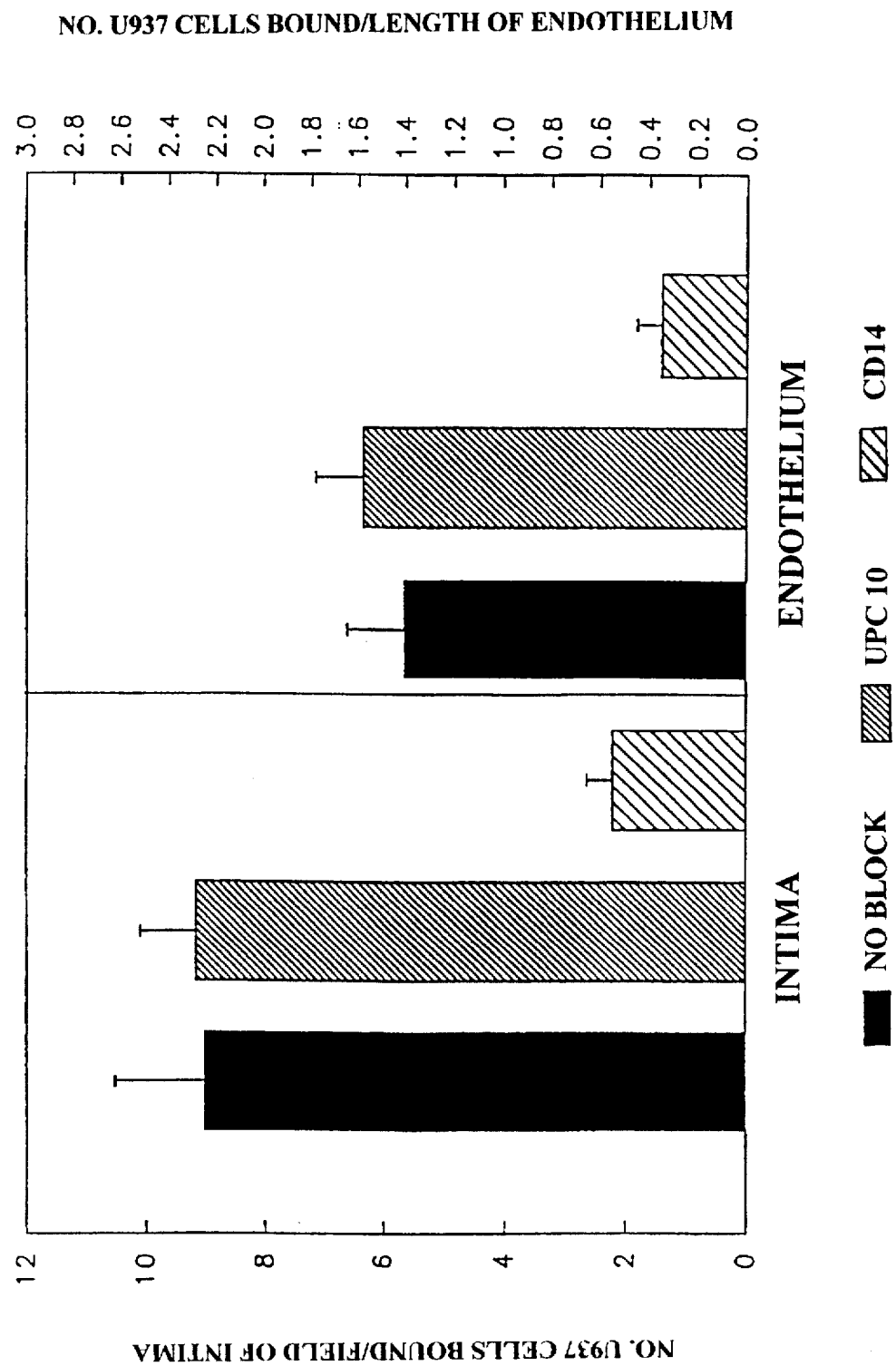

LEUKOCYTE ADHESION ASSAY

The present invention relates to a leukocyte-adhesion assay, more particularly a method of assaying leukocyte binding to vascular tissue.

Atherosclerosis is a disease of the arteries which results in approximately half of the total deaths in Western countries. The disease involves thickening of the inner part (intima) of the artery wall by infiltration of monocytes (a type of leukocyte normally present in the blood). Following infiltration, the monocytes mature into large cells called macrophages, which is followed by the accumulation of cholesterol, first within the macrophages but later becoming more widespread. Smooth muscle cells also appear and proliferate, probably under the influence of growth factors released by the macrophages. All of these components contribute to the thickening of the artery wall reducing the passage of blood through the artery which may finally become blocked by a blood clot forming at the site.

In recent years much has been learned about the mechanisms by which monocytes and other types of leukocytes migrate from the blood into tissues suffering from inflammation. One such mechanism involves adhesion molecules present on the inner surface of the vessels at sites of inflammation. The inner surface of all blood vessels consists of thin delicate cells referred to as endothelial cells and these form protein adhesion molecules which are able to bind specifically to receptors on leukocytes. These receptors are themselves adhesion molecules and consist of either carbohydrates, proteins or sulphur compounds on the surface of the leukocyte. Leukocytes can also be bound by other cells and structures within tissues by a number of similar adhesion interactions.

Recent work has shown that certain adhesion molecules are present on the endothelial cells of the diseased parts of atherosclerotic arteries but not in the normal parts of these arteries (see Poston et al, Am. J. Pathol., 140(3), 665–673 (1992)). One adhesion molecule (ICAM-1) also appears on smooth muscle cells within the thickened area but is not seen on these cells elsewhere. These observations suggest that atherosclerotic lesions may resemble foci of inflammation and that monocytes leave the blood under the influence of adhesion molecules entering and adding to the disease process.

Whatever the precise mechanism, it is clear that the adhesion of leukocytes, and particularly monocytes, to the arterial wall plays an important role in the development of atherosclerotic lesions. For this reason, there is a need for a method of assaying leukocyte binding to vascular tissue.

One method which has previously been used for studying the binding of leukocytes to tissue is the so-called Stamper-Woodruff assay. This assay was developed originally to study the mechanism of lymphocytes binding to lymph nodes (Stamper & Woodruff, J. Exp. Med., 144, 828–833 (1976)). A suspension of rat thoracic duct lymphocytes in RPMI medium was contacted at about 7° C. with thin sections of rat or mouse lymph node tissue, bound cells were fixed and visualised and then identified under a light microscope.

The assay has subsequently been used in other applications and, for example, a modified version was used to investigate experimental autoimmune encephalomyelitis which is an inflammatory condition of the nervous system with similarities to multiple sclerosis (Yednock et al, Nature, 356, 63–66 (1992)). A suspension of a human monocytic cell line (U937) in RCMI medium was contacted with thin sections of brain tissue from normal rats and rats suffering from experimental autoimmune encephalomyelitis, bound cells were fixed and visualised and then identified under a light microscope. The brain tissue was generally contacted with U937 cells on ice although there is reference to some experiments having been carried out at 25° C.

It has now been found that a version of the Stamper-Woodruff assay can be applied to provide a functional assay for leukocyte adhesion to vascular tissue, for example tissue derived from atherosclerotic lesions.

The present invention provides a method of assaying leukocyte binding to vascular tissue which comprises contacting a suspension of a monocyte-like cell line in a suitable medium with a human vascular tissue sample at a temperature of at least 10° C., and quantitating the number of bound cells over a defined area of tissue sample.

In principle, the method according to the invention can be applied to any vascular tissue although the method is particularly applicable to assaying the binding of monocytes to atherosclerotic human artery. Generally, the tissue will be prepared as a thin section by standard histological procedures for example forming a cryostat section. The thickness of the section is preferably up to about 30 μm, more preferably up to about 10 μm, most preferably about 5 μm.

The section of tissue is mounted on a microscope slide. Preferably aminopropyl triethoxysilane (APES) coated slides are used to improve adhesion of the sections, (see Maddox & Jenkins, J. Clin. Pathol., 40, 1256–1257 (1987)). Although a chemical fixation procedure can be applied if desired, the sections are preferably used in the assay without any previous chemical fixation procedure.

Any monocyte-like cell line can used in the method according to the invention. A monocyte-like cell line is a cell line which has adhesion properties similar to human monocytes so that it adheres to vascular tissue (for example arterial wall) in a similar manner to human monocytes. The adhesion properties of monocytes are, in turn, determined by the adhesion receptors on the surface of the cell.

The monocyte-like cell line is preferably a monoclonal cell line. One particularly preferred monocyte-like cell line is the U937 histiocytic lymphoma cell line according to Harris & Ralph, J. Leukocyte Biol., 37, 407–422 (1985) available to the public from ATCC number CRL 1593. The U937 cell line was first described by Sundstrom and Nilsson (Int. J. Cancer, 17, 565–577 (1976)). An alternative monocyte-like cell line is the THP-1 monocyte cell line available to the public from ATCC number TIB 202 (see Tsuchiya et al Int. J. Cancer, 26, 171 (1980)).

The above monoclonal monocyte like cell lines can be grown by standard methods in cell culture medium such as RPMI medium and will generally be used according to the invention in suspension in that or a similar medium. In the case of the U937 cell line, a preferred cell culture medium is RPMI medium containing 10% fetal calf serum and this medium can also be used for the assay but preferably containing 10 mM HEPES buffer. The monoclonal monocyte like cells are preferably activated in order to increase adhesion, for example by use of a phorbol ester. According to one embodiment of the invention U937 cells can be activated by use of phorbol myristyl acetate, for example suspension in tissue culture medium containing 10 ng/ml phorbol myristyl acetate for 24–48 hours at 37° C.

Whilst monoclonal cell lines are preferred, normal human monocytes can also be used in the application of the method, according to the invention. Normal human monocytes can be prepared from heparinised human blood by centrifuging on a Ficoll-Hypaque density gradient to isolate mononuclear leukocytes, followed by adhesion to plastic tissue culture flasks. Alternatively, monocytes can be isolated from blood in an elutriation apparatus. Furthermore, by use of monocytes derived from patients' blood, the assay can also be employed to assess the adhesive properties of monocytes in patients with atherosclerotic or other disease.

A suitable concentration of cells for contacting with the vascular tissue sample is about $10^6$ to $10^8$ cells per ml, preferably about $10^7$ cells per ml.

The section of vascular tissue is contacted with the monocyte-like cell suspension under conditions and for a sufficient length of time which allow the cells to adhere to the vascular tissue where suitable adhesion molecules are present to bring about such adhesion. Preferably a section of vascular tissue on a microscope slide is contacted with the cell suspension on a rotating table at a rotation speed of about 40 to 80 rpm, preferably about 60 rpm. The time of contact may be very short or may be up to about 1 hour or longer, preferably about 40 minutes.

As noted above, in the past the Stamper-Woodruff assay has generally been carried out at low temperature, i.e. around 4° to 7° C. Surprisingly, it has been found that the assay according to the present invention is inoperative at 4° C. in that no binding takes place at this temperature. Accordingly, the assay should be carried out at a temperature of at least 10° C., for example about 15° to 45° C., preferably about 20° to 40° C., more preferably about 37° C.

After contact with the suspension of monocyte-like cells, the vascular tissue sample may be treated by standard histological techniques to bring the sample into a condition where the number of bound monocyte-like cells may be quantitated. Thus the sample may be washed for example using phosphate buffered saline at low temperature, for example 4° C., and then fixed for example using paraformaldehyde or glutaraldehyde.

Finally, the samples are stained in a suitable manner, for example using haemotoxylin, and the binding of monocyte-like cells can then be observed under a microscope. Recognition can be facilitated by performing izmunohistochemical staining for monocyte associated antigens, e.g. CD15. Under the microscope bound cells can be distinguished from calls in the section itself by being rounded and lying in a different focal plane. The number of bound monocyte-like cells can be quantitated by counting the number of cells in a defined area of sample either manually or automatically. Automatic counting can be effected by the use of image analysis equipment programmed to recognise objects of the size and circularity of the adherent cells, for example the image analyser produced by Sight Systems (Hove, U. K.).

The assay according to the present invention is valuable for a number of purposes. Thus the involvement of adhesion molecules in the entry of monacytes into atherosclerotic foci may be of profound significance as it appears to be a vital mechanism in this initial event in the generation of the disease. There is reason to suppose that once monocyte entry has started, it may be self-perpetuating, as factors produced by the monocyte-derived macrophages may elicit further formation of endothelial adhesion molecules. As well as providing a means of investigating the mechanism of monocyte entry, the method according to the invention has important uses in the development of therapeutic approaches to the treatment of atherosclerosis.

The assay can be used for the investigation of inhibitors of the adhesion process. For example EDTA or EGTA remove divalent cations and thereby inhibit the interaction of monocytes with the endothelium. The interaction may also be inhibited at least in part by peptides containing the Arg-Gly-Asp sequence, a property which is associated with adhesion through the leukocyte adhesion molecules referred to as integrins. Adhesion may also be inhibited by certain carbohydrate binding proteins such as the lectin, wheat germ agglutinin, and by a number of antibodies, in particular monoclonal antibodies, directed against various adhesion molecules. This suggests that carbohydrates may also have potential as binding inhibitors.

Agents that can inhibit the process of adhesion of monocytes to the intima are candidates for use as therapeutic agents against human atherosclerosis. The method according to the present invention can be used for screening possible inhibitory agents with the potential for the development of therapeutic approaches against human atherosclerosis. Assay for adhesion of monocyte-like cells in the presence and the absence of a potential inhibitory agent will identify those agents which inhibit the adhesion process. Alternatively the cell suspension or the tissue section can be preincubated with a potential inhibitory agent.

Thus, according to another aspect, the present invention provides a method of identifying agents which inhibit binding of monocytes to human vascular tissue which comprises carrying out the assay defined above in the presence and in the absence of a potential inhibitory agent or with or without preincubation of the cell suspension or the tissue with a potential inhibitory agent, and assessing the effect of the agent on the extent of monocyte binding. The invention also provides agents for use in the therapy of atherosclerosis identified in this way.

A further application of the assay according to the invention is in conjunction with animal models for human atherosclerosis. Thus, use can be made of the assay to compare the effects of a range of agents on the binding of monocyte-like cells to human vascular tissue (particularly tissue from human atherosclerotic lesions) with their effect on the binding to tissue (again particularly atherosclerotic lesions) from another species, for example the rabbit. Use of the assay according to the invention would indicate whether an agent found to be effective in inhibiting experimentally induced atherosclerosis in another species would be likely also to be effective in man.

In carrying out the assay according to the invention as described above, binding of monocytes is observed to the intima as well as the endothelium. It is likely that endothelial adhesion depends on different adhesion reactions from intimal binding. In this event, the assay according to the invention can be made specific for endothelial binding, which may be critical to monocyte entry, by carrying out the assay in the presence of an inhibitor which selectively blocks intimal binding.

Results obtained using the assay according to the present invention have indicated for the first time the involvement of the monocyte cell surface molecule CD14 in atherosclerosis. In particular it has been found that an anti-CD14 antibody UCHM-1 (see below) gave strong inhibition of binding of U937 cells to atherosclerotic lesions. This suggests a potential utility for agents which inhibit CD14 dependent monocyte adhesion in the treatment of atherosclerosis. Suitable agents include antibodies against CD14 and other molecules, e.g. small chemical molecules, which inhibit CD14 dependent monocyte adhesion. It may be possible to use rodent antibodies against CD14, for example UCHM-1 or OM1, in a therapeutic context. UCHM-1 is widely available commercially, for example from Sigma, and is described by Hogg et al, Immunology, 53, 753 (1984). OKM1 is also available to the public, for example from the ATCC, deposit number CRL 8026. Other anti-CD14 antibodies are available or can be derived using known methods. However, it is preferred to develop anti-CD14 antibodies which have less potential for eliciting a reaction from the human immune system using known techniques such as the production of chimeric or humanised (e.g. CDR-grafted) antibodies. It is more preferred in a therapeutic context to use small chemical molecules, for example molecules with a molecular weight up to about 1000.

According to another aspect, the present invention provides the use of an agent which inhibits CD14 dependent monocyte adhesion for the manufacture of a medicament for the treatment or prevention of atherosclerosis.

According to a further aspect, the present invention provides a method for the treatment or prevention of atherosclerosis which comprises administering to a patient an effective amount of an agent which inhibits CD14 dependent monocyte adhesion.

In some cases, it may be possible to administer an agent which inhibits CD14 dependent monocyte adhesion to a patient as the raw substance but the agent will generally be presented as a pharmaceutical composition. In this context a pharmaceutical composition comprises at least one agent which inhibits CD14 dependent monocyte adhesion (referred to herein as the "active ingredient") with one or more pharmaceutically acceptable carriers or diluents. The carrier(s) or diluent(s) must be "acceptable" in the sense of not having any deleterious effect on the patient and being compatible with other components of the formulation. The pharmaceutical composition may also contain other therapeutic ingredients having the same or a different therapeutic effect from the active ingredient, for example agents having an effect on the heart or circulation, such as anti-coagulants or anti-hypertensives.

In the case of small chemical molecules, the active ingredient may be formulated for administration by any suitable means provided that it is delivered to the circulation in such a-manner that CD14 monocyte adhesion in the vicinity of atherosclerotic plaque or at potential sites of atherosclerotic plaque formation can be inhibited. Examples of suitable forms of administration include oral, parenteral, rectal or intranasal, e.g. by inhalation.

A pharmaceutical composition for oral administration may take the form of, for example, tablets or capsules and may be prepared by processing the active ingredient in a conventional manner together with one or more pharmaceutically acceptable excipients. Tablets may be prepared by compression or moulding in known manner and suitable excipients include binding agents, fillers, lubricants, disintegrants and wetting agents. Tablets or capsules may be coated in known manner, for example to provide slow or controlled release of the active ingredient.

Liquid preparations for oral administration may take the form, for example, of solutions, syrups or suspensions or may be presented as a dry product for re-constitution with water or another suitable vehicle prior to use.

Compositions for parenteral administration include aqueous and non-aqueous sterile injection solutions which may be formulated in known manner. The formulations may be presented in unit-dose or multi-dose containers, for example, ampoules or vials, or may be stored in a lyophilised condition suitable for reconstitution by addition of sterile liquid, for example water for injection.

Compositions for rectal administration may be presented in forms such as suppositories or retention enemas which may be formulated in known manner.

Compositions for intranasal administration may be formulated as solutions for administration via a metered dose or unit device or as a powder including a suitable carrier for administration using an appropriate delivery system.

Antibodies which inhibit CD14 dependent monocyte adhesion will generally also be administered to patients in the form of a pharmaceutical composition which preferably includes, in addition to the antibody, a physiologically acceptable carrier or diluent, possibly in admixture with one or more other agents such as other antibodies or drugs, such as antibiotics or agents having an effect on the heart or circulation. Suitable carriers include physiological saline and phosphate buffered saline. Alternatively the antibody may be lyophilised and reconstituted before use by the addition of an aqueous buffered solution. Routes of administration of the antibody include intravenous, intramuscular, subcutaneous and intraperitoneal injection or delivery.

The method by which the agent which inhibits CD14 dependent adhesion is used in the treatment or prevention of atherosclerosis will depend on the nature of the agent. Small chemical molecule may be used prophylactically over long periods by subjects at risk of atherosclerosis. Antibodies carry more risk of an adverse reaction from the subjects immune system and are more suitable for short term therapy of patients at particular risk in special circumstances, for example following heart transplantation. In all cases the precise dose to be administered will be at the discretion of the attendant physician but will depend on the nature of the agent and a number of other factors including the age and sex of the patient, the condition of the patient and the severity of the disorder being treated.

The invention is further described with reference to the following Examples and drawings described below.

DESCRIPTION OF THE DRAWINGS

The invention is described further with reference to the following Examples. In the examples, reference is made to the accompanying drawings in which:

FIG. 3 shows the affect of CD14 and control antibodies on U937 cell adhesion.

EXAMPLE 1—ASSAY PROTOCOL

Figure 1:
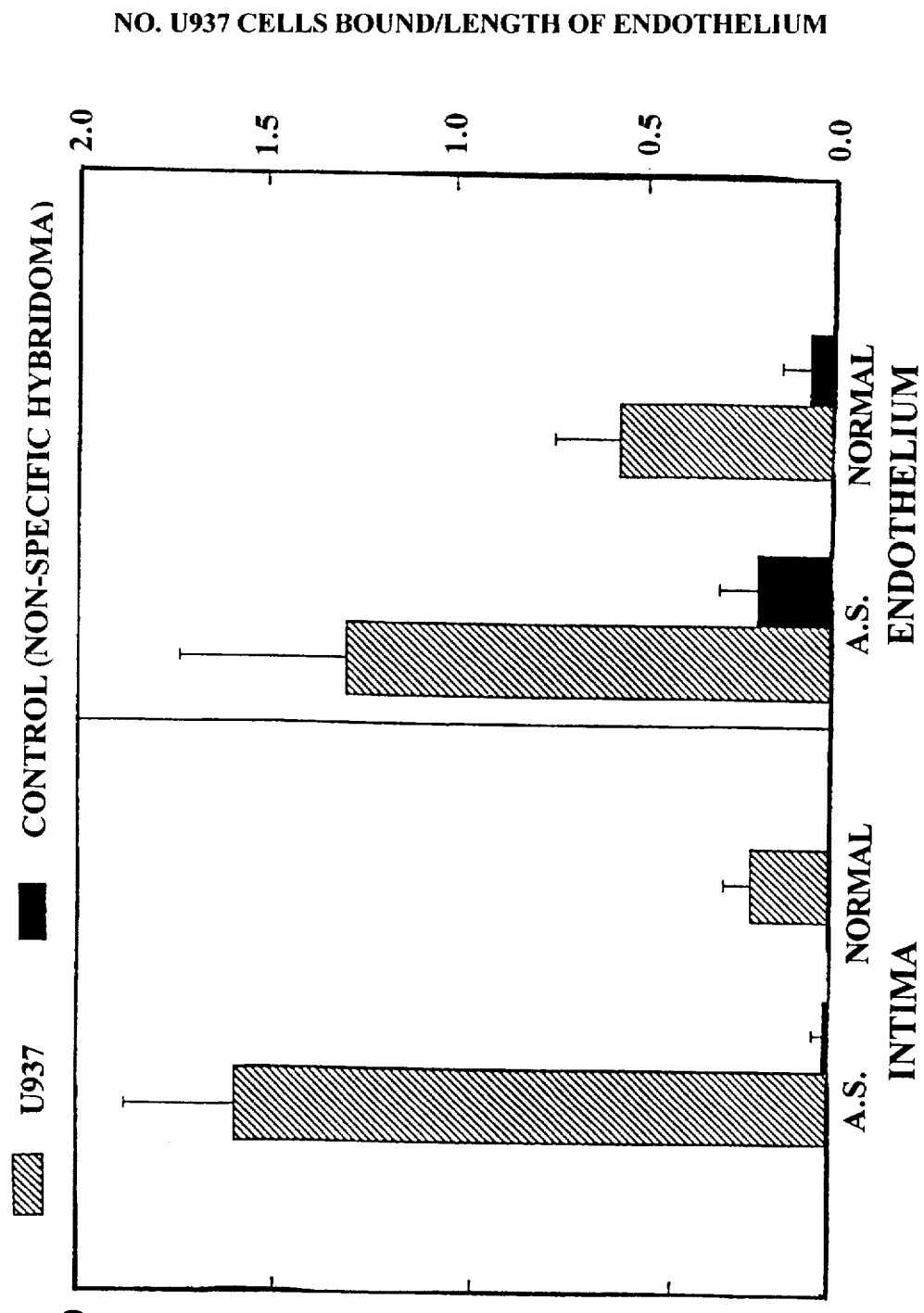
FIG. 1 shows U7937 and control hybridoma cell binding to atherosclerotic and normal tissue.

Samples of vascular tissue, such as atherosclerotic plaque, of dimensions up to about 8 mm, are snap frozen by immersion in isopentane cooled in liquid nitrogen. Sections of the tissue, 5 µm thick are cut with a cryostat and mounted onto aminopropyltriethoxysilane (APES) coated microscope slides. A ring is optionally drawn round the section on the slide using a felt-tip pen containing a hydrophobic compound (Dako Ltd., High Wycombe, U. K.). The sections are used fresh in the assay, i.e. without chemical fixation and within one hour of cutting.

U937 cells (ATCC no. CRL 1593) are cultured in RPMI-1640 tissue culture medium with 10% fetal calf serum. They are harvested by centrifugation at 1000 rpm and resuspended in 10 ng/ml of phorbol myristyl acetate (PMA) for 24–48 hours at 37° C. This results in activation of the cells and increased adhesion. Studies can be done with or without the activation stage.

U937 cells are separated from the surface of the tissue culture flask by agitation, then centrifuged down, counted and adjusted to $10^7$ cells/ml in RDMI-1640 medium containing 10% fetal calf serum and buffered with 10 mM HEPES buffer.

200 µl of the cell suspension is placed on the slide (within the marker ring if this is used) and the slide is immediately placed on a rotating table turning at 60 rpm and maintained at 37° C. The section is incubated under these conditions for 40 minutes. The section is then washed by gently dipping 5 times into a bath of ice cold phosphate buffered saline. Adhered U937 cells are then fixed by incubating for 10 minutes in 4% paraformaldehyde on ice. The section is washed in water, stained with Mayer's haematoxylin for 2 minutes, washed, dehydrated through alcohol and toluene baths and mounted in DPX mountant (BDH) in a routine histological manner (see for example Theory and Practice of Histological Techniques, Bancroft & Stevens, Churchill Livingstone, 1990).

Binding of U937 cells can be observed under a microscope and bound cells can be distinguished from cells in the section itself by being rounded and lying in a different focal plane. Binding can be quantitated by counting cells in multiple microscope high power fields over histologically defined areas of the specimen.

For assessment of the binding to atherosclerotic plaque, the number of cells binding to the intimal layer of plaques and control normal intimal areas of human artery wall can be counted. To quantitate endothelial adhesion, U937 cells contacting or overlying the endothelial cell layer can be assessed. If necessary, the layer can be recognised by the immunohistochemical staining of the section for von Willebrand factor after the fixation stage, (see Poston et al, Amer. J. Pathol., 140, 665–673 (1992)).

EXAMPLE 2—BINDING TO ATHEROSCLEROTIC PLAQUE

Sections of atherosclerotic plaque were assessed to define the nature and extent of lesions and their subtype in the atherosclerotic spectrum. Lesions were subdivided into fatty streaks, fibro-fatty plaques, complex lesions and fibrous lesions. The method of assessment was by histology aided by immunohistochemistry with antibodies to macrophages, smooth muscle cells, and endothelium. These procedures have been described previously (see Poston et al, Am. J. Pathol., 140(3), 665–673 (1992)). Staining of the endothelium with antibody to von-Willebrand factor is particularly useful in defining the integrity of the layer, and quantitation, as described below, was only performed in those areas that were demonstrably intact. Furthermore the same assessment defined areas that were histologically normal, and these were used as controls. The results described below were obtained with PMA stimulated U937 cells.

In the assessment of the binding of U937 cells to atherosclerotic plaque, the number of cells binding was quantitated in two histological areas as follows:

1) Endothelium:—A cell was counted as being adherent to the endothelium if the cell was over the endothelial layer or adherent to the luminal margin. The whole length of the intact endothelium over a plaque was counted, consisting of 10–30 high power fields (HPF), and results expressed either as cells per high power field (as below), or as cells per length of endothelium.

2) Intima:—The intimal area to be counted was defined as the layer extending from immediately beneath the endothelium to the internal elastic lamina. Ten random high power fields were chosen, and results expressed as mean value per HPF.

RESULTS

This assay demonstrated a highly selective binding of U937 cells to the endothelium and whole intimal layer of atherosclerotic plaque. Binding of U937 cells to the free border of the endothelium was often apparent. Much less was found in normal areas of artery. Some medial binding was also seen in association with the plaques. Levels of binding varied considerably from one lesion to another, and were reproducible. Negligible binding occurred if the assay was performed at 4° C., compared to the usual 37° C.

In an assessment of 13 atherosclerotic arteries (fibro-fatty plaques) and 6 normal controls, $3.04\pm2.51$ cells/HPF (mean±SD) were bound to the endothelium of plaques, compared to $0.58\pm0.42$ over the endothelium of normal artery, p=0.0075, Mann-Whitney U test.

In the intimal layer, $16.1\pm10.2$ cells/HPF were bound in the atherosclerotic specimens, compared to $1.3\pm1.1$ cells/HPF in the normal arteries, p=0.0025.

By contrast, a B lymphocyte/myeloma hybridoma cell line used as a control gave only 0.11 and 1.18 cells/HPF bound in the atherosclerotic endothelial and intimal regions respectively, and less in the normal areas. These results are shown in FIG. 1, in which the shaded bars are the results of binding of U937 cells and the blocked bars are control (non-specific hybridoma).

Figure 2:
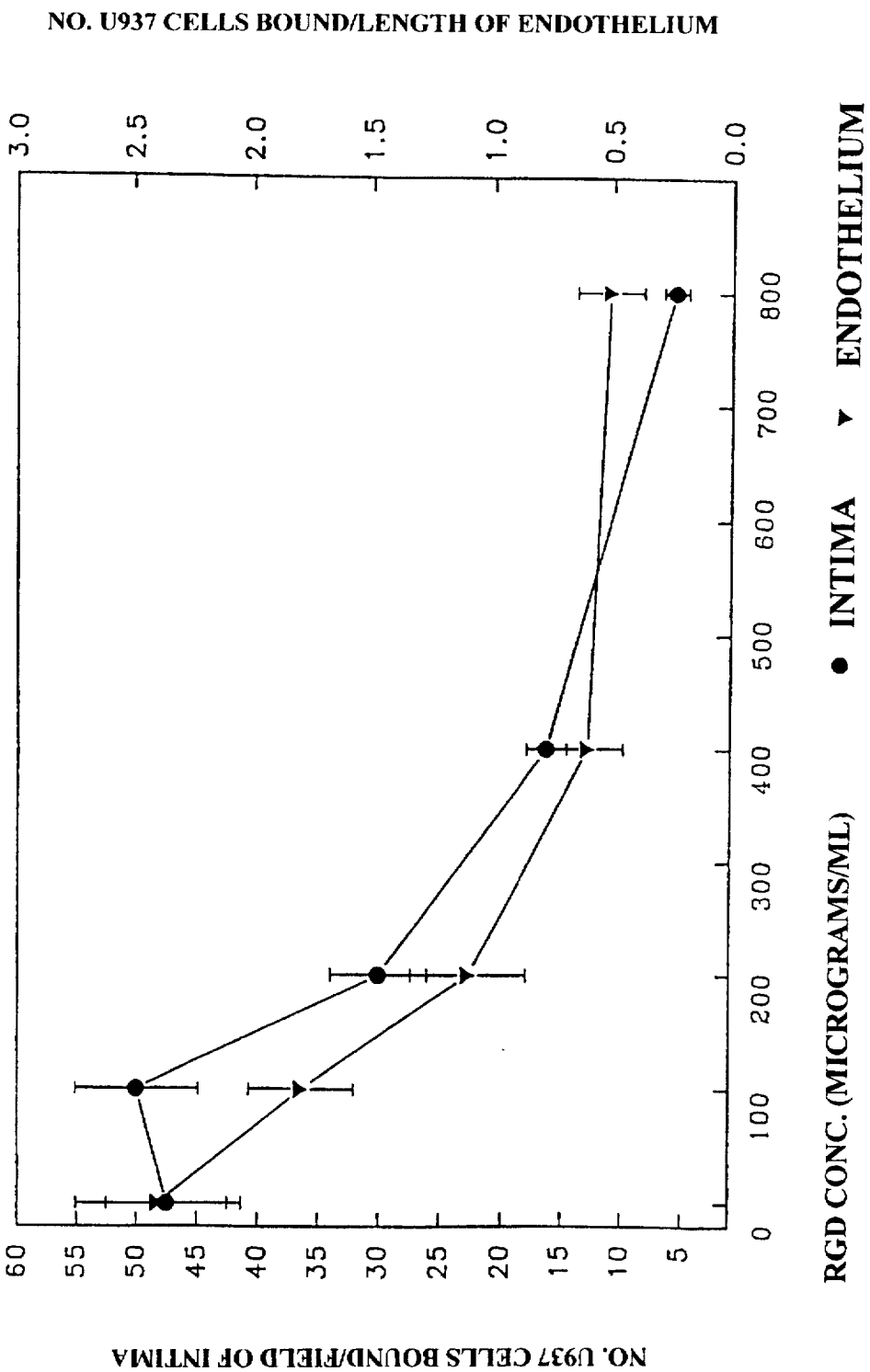
FIG. 2 shows the affect of Arg-Gly-Asp peptides on U937 cell adhesion.

In the assessment of inhibitory substances, endothelial and intimal binding behaved in a similar manner. EGTA and EDTA caused total inhibition of binding. This is compatible with the involvement of selectin or integrin adhesion molecules in the process, as both are known to be divalent cation dependent. Likewise wheat-germ agglutinin, which binds N-acetyl glucosumine, caused a marked decrease in binding. An involvement of sugar residues is therefore probable. The peptide Gly-Arg-Gly-Asp-Ser (Sigma) caused dose-related inhibition of adhesion (FIG. 2), again suggesting the involvement of integrins, which bind peptides containing the Arg-Gly-Asp sequence. In FIG. 2 the circles show binding to the intima and the triangles binding to the endothelium. Antibodies to the $\beta_1$ and $\beta_2$ integrin chains (CD29 and CD18) gave inhibition, but an antibody to the endothelial adhesion molecule ICAM-1 had only & weak effect. An antibody UCHM-1 (20 µg/ml) to a monocyte cell surface molecule, CD14, gave strong inhibition of binding (FIG. 3), as compared to no blocking and to a control immunoglobulin (UPC10, 20 µg/ml). In FIG. 3 the blocked bars are no blocking, the closely spaced shaded bars are control antibody and the wider spaced shaded bars are anti-CD14 antibody. UCHM-1 and UPC10 are both mouse immunoglobulins of the same class ($IgG_{2a}$). The CD14 molecule has recently been found to mediate monocyte-endothelial adhesion (see Beekhuizen and Van Furth, J. Leukocyte Biol., 54, 363–378 (1993)). These experiments suggest that integrins, carbohydrates, CD14, and possibly selectins are involved in the adhesion reactions identified.

I claim:

1. A method of assaying leukocyte binding to a tissue sample which comprises contacting an arterial tissue sample section at a temperature of at least 10° C. with a suspension in a medium of monocytes or a cell line having adhesion to arterial tissue similar to monocytes, and quantitating the number of bound cells over a defined area of tissue sample section.

2. A method according to claim 1 wherein the arterial tissue is derived from atherosclerotic artery.

3. A method according to claim 2 wherein the arterial tissue is human.

4. A method according to claim 1 wherein the monocytes or cell line is contacted with the arterial tissue sample at a temperature of about 15° to 45° C.

5. A method according to claim 1 wherein the arterial tissue sample section comprises a cryostat section.

6. A method according to claim 1 wherein the cell line is a monoclonal cell line.

7. A method according to claim 1 using human monocytes derived from the blood of an individual having or suspected of having atherosclerotic or other disease.

8. A method according to claim 1 wherein the monocytes or cell line are contacted with the arterial tissue sample in suspension in cell culture medium.

9. A method according to claim 1 wherein the monocytes or cell line are contacted with the arterial tissue sample at a concentration in the medium of $10^6$ to $10^8$ cells per ml.

10. A method according to claim 9 wherein the concentration is about $10^7$ cells per ml.

11. A method according to claim 1 wherein the arterial tissue sample section is mounted on a microscope slide.

12. A method according to claim 11 wherein the microscope slide is mounted on a rotating table and rotated at a rotation speed of about 40 to 80 rpm.

13. A method according to claim 12 wherein the rotation speed is about 60 rpm.

14. A method according to claim 1 wherein the contact time is up to 1 hour.

15. A method according to claim 14 wherein the contact time is about 40 minutes.

16. A method according to claim 1 wherein following contact with the arterial tissue sample the cells are fixed with paraformaldehyde or glutaraldehyde to yield a fixed sample.

17. A method according to claim 16 wherein the fixed sample is stained.

18. A method according to claim 17 wherein the fixed sample is stained with haemotoxylin.

19. A method according to claim 17 wherein the fixed sample is stained by an immuno-histochemical procedure.

20. A method according to claim 1 wherein the number of bound cells is quantitated by manual counting under a microscope.

21. A method according to claim 1 for identifying an agent which inhibits binding of monocytes to arterial tissue which comprises carrying out successive assaying determinations on said arterial tissue sample section under conditions which correspond to one another except for a differential condition selected from the group consisting of (i) the presence and in the absence of a potential inhibitory agent, and (ii) with and without preincubation of the monocytes or the tissue with a potential inhibitory agent, and assessing the effect of the agent on the extent of monocyte binding.

22. Use of an agent which inhibits CD14 cell surface antigen dependent monocyte adhesion for the manufacture of a medicament for the treatment or prevention of atherosclerosis.

23. Use according to claim 22 wherein the agent is a chemical molecule with a molecular weight up to about 1000.

* * * * *